(12) United States Patent
Bekenstein et al.

(10) Patent No.: US 11,225,661 B2
(45) Date of Patent: Jan. 18, 2022

(54) METHODS FOR CONTROLLING SEIZURES BY MANIPULATING THE LEVELS OF MICRORNA-211 (MIR-211) IN THE BRAIN

(71) Applicant: Uriah Bekenstein, Rehovot (IL)

(72) Inventors: Uriah Bekenstein, Rehovot (IL); Hermona Soreq, Jerusalem (IL); David Greenberg, Jerusalem (IL)

(73) Assignee: Uriah Bekenstein, Rehovot (IL)

( * ) Notice: Subject to any disclaimer, the term of this patent is extended or adjusted under 35 U.S.C. 154(b) by 0 days.

(21) Appl. No.: 16/365,667

(22) Filed: Mar. 26, 2019

(65) Prior Publication Data
US 2020/0102559 A1    Apr. 2, 2020

Related U.S. Application Data

(60) Provisional application No. 62/640,139, filed on Mar. 8, 2018.

(51) Int. Cl.
| | |
|---|---|
| *C12N 15/11* | (2006.01) |
| *C12N 15/113* | (2010.01) |
| *A61P 25/08* | (2006.01) |
| *A01K 67/027* | (2006.01) |

(52) U.S. Cl.
CPC ........ *C12N 15/113* (2013.01); *A01K 67/0275* (2013.01); *A61P 25/08* (2018.01); *A01K 2217/05* (2013.01); *A01K 2227/105* (2013.01); *A01K 2267/0356* (2013.01); *C12N 2310/113* (2013.01); *C12N 2310/141* (2013.01); *C12N 2310/3231* (2013.01)

(58) Field of Classification Search
CPC ............ C12N 15/113; C12N 2310/113; C12N 2310/3231; C12N 2310/141
See application file for complete search history.

(56) References Cited

U.S. PATENT DOCUMENTS

| | | | |
|---|---|---|---|
| 9,803,200 B2 | 10/2017 | Henshall et al. | |
| 2013/0210901 A1* | 8/2013 | Soreq ...................... | C07H 21/02 514/44 R |

FOREIGN PATENT DOCUMENTS

| | | | | |
|---|---|---|---|---|
| WO | WO-2014096418 A2 * | 6/2014 | ......... | A61K 31/7088 |

OTHER PUBLICATIONS

Bekenstein et al., miR-211 is a neuronal regulator of cholinergic-induced seizures, Journal of Neurochemistry, Aug. 2017, vol. 142, No. Suppl 2, p. 206 (Year: 2017).*
Chu et al., miR-211 promotes the progression of head and neck carcinomas by targeting TGFβRII, Cancer Letters, 2013, 337: 115-124 (Year: 2013).*
Temkin et al., Stress as a Risk Factor for Seizures Among Adults with Epilepsy, Epilepsia, 1984, 25, 4: 450-456 (Year: 1984).*
French, Refractory Epilepsy: Clinical Overview, 2007, Epilepsia, 48 (Suppl.1): 3-7 (Year: 2007).*
Pitkanen et al., Epilepsy Related to Traumatic Brain Injury, Neurotherapeutics, 2014, 11: 286-296 (Year: 2014).*
Bekenstein U et al."Dynamic changes in murine forebrain miR-211 expression associate with cholinergic imbalances and epileptiform activity" Proceedings of the National Academy of Sciences of the United States of America. Jun. 20, 2017.
Lim Lee P. et al.,"Vertebrate microRNA genes" Science, vol. 299, Mar. 7, 2003.
Chen J, et al. "A functional variant in the 3'-UTR of angiopoietin-1 might reduce stroke risk by interfering with the binding efficiency of microRNA 211" Human Molecular Genetics, vol. 19, No. 12, Jun. 15, 2010.
Levy C, et al. "Intronic miR-211 assumes the tumor suppressive function of its host gene in melanoma" Molecular Cell. Dec. 10, 2010.
Maluf DG, et al. "MicroRNA profiles in allograft tissues and paired urines associate with chronic allograft dysfunction with IF/TA" American Journal of Transplantation Oct. 11, 2011.
Ma Y. "The Challenge of microRNA as a Biomarker of Epilepsy" Current Neuropharmacology. 2018.
Henshall DC, et al. "MicroRNAs in epilepsy: pathophysiology and clinical utility" Lancet Neurology. Dec. 15, 2016.
Jimenez-Mateos EM, et al. "Antagomirs targeting microRNA-134 increase hippocampal pyramidal neuron spine volume in vivo and protect against pilocarpine-induced status epilepticus" Brain Structure and Function, vol. 4, Jul. 2015.
Henshall DC. "MicroRNAs in the pathophysiology and treatment of status epilepticus" Frontiers in Molecular Neuroscience, Nov. 12, 2013.
Goll Y, et al. "Sustained Alzheimer's amyloid pathology in myeloid differentiation protein-88-deficient APPswe/PS1 mice" Neurodegenerative Diseases. Oct. 30, 2013.
Griffiths-Jones S, et al. "miRBase: microRNA sequences, targets and gene nomenclature" Nucleic Acids Research, vol. 34. Oct. 18, 2005.

* cited by examiner

*Primary Examiner* — Ekaterina Poliakova-Georgantas
(74) *Attorney, Agent, or Firm* — The Roy Gross Law Firm, LLC; Roy Gross

(57) ABSTRACT

Method for controlling for the appearance of seizures in the mammalian brain comprising modifying the abundance of a specific miRNA—miR-211, for uses in preventing seizures and providing a model system to examine the effect of a drug or a treatment to seizures.

15 Claims, No Drawings
Specification includes a Sequence Listing.

METHODS FOR CONTROLLING SEIZURES BY MANIPULATING THE LEVELS OF MICRORNA-211 (MIR-211) IN THE BRAIN

RELATED APPLICATIONS

This application claims priority to U.S. Provisional Patent Application No. 62/640,139 filed Mar. 8, 2018, the contents of which is fully incorporated herein by reference.

FIELD OF THE INVENTION

The present invention relates in general to modeling or treatment of seizures or epilepsy.

The invention more specifically relates to changing the expression level or availability of microRNA-211 in the mammalian brain, such as for treatment of seizures and seizure-related conditions, as well as for modeling increased susceptibility for seizures in model organisms.

BACKGROUND OF THE INVENTION

Epilepsy is a chronic neurological disorder characterized by the occurrence of unprovoked seizures. Epilepsy affects over 50 million people worldwide, with one third of these cases considered unsatisfactorily-controlled by current treatments (Pitkanen, Loscher et al. 2016). With a high lifetime prevalence of about 1% of the population (Coon, Siegel et al. 2006). Therapeutics for this prevalent malady is called for.

MicroRNAs (miRNAS, miRs) are small non-coding RNA molecules, conserved thought the animal kingdom as well as in plants. In mammals, miRs regulate the expression levels of most protein coding genes—orchestrating whole transcriptional pathways (Levy, Khaled et al. 2010).

MiR-211 is an intra-genic miRNA located within an intron of the gene melastatin, in both mice and men. It was acknowledged to play the tumor suppressor role presumed for melastatin. And is studied extensively in the context of Melanoma. MiR-211 was also found to regulate the choice towards apoptosis in cells under ER stress in check—as in stressed cells PERK induced miR-211 expression, which in turn attenuated stress-dependent expression of the pro-apoptotic chop/gadd153 transcription factor (Chitnis, Pytel et al. 2012), and to play a role in neuronal differentiation, with suggested implications to the biochemistry of Alzheimer's disease (Fan, et al. 2016).

We noted (and perused) miR-211 as a candidate in a search for miRs that may relate to seizures and provide new experimental evidence and systems that show miR-211 modification in the mammalian brain effects hyper-synchronization and excitability reminiscent of brain seizure.

SUMMARY OF INVENTION

In one aspect, the present invention provides that miR-211 is expected to be potent as a regulator of neuronal functions relating to seizures. With its location in the 15q13.3 locus (epilepsy related) we found miR-211 to be of specific interest, and even more as we found that it in-vitro targets the UTR of nAChRα7—a gene in which a gain-of-function mutation results in nicotine-induced seizures.

In an additional aspect, the present invention provides that spontaneous seizures arise in mice with miR-211 dox-controlled expression, which is confined to the brain—following abrupt reduction in miR-211 levels.

The present invention also provides that these seizures concord with directional gene expression changes of cholinergic synaptic receptors, and to changes in the level of miR-134. Thus providing by convergent experimental evidence that modification of miR-211 levels in the brain effects the susceptibility to seizures.

In an additional aspect, the present invention provides that increased susceptibility to a convulsant is rendered by brain reduction of miR-211 levels.

In an additional aspect the present invention provides that separate transgenic mice model with overexpressed modified cholinergic receptor the miR-211 is altered alongside seizure related phenotypes. In an additional aspect, the present invention provides that in both mice and men miR-211 relates to phenotypes and Abeta-related pathologies (pertinent to Alzheimer's disease) and memory impairments.

Altogether the invention provides that preventing miR-211 reduction in the brain of mammals reduces the threshold for seizures and seizure related convulsions—pertinent for use in both therapy as well as in modeling seizure for research.

DETAILED DESCRIPTION OF THE INVENTION

The present invention is substantially based on the findings (described below) in humans and mice:

We noted miR-211 using a "oblique angle" functional strategy: aiming to find miRNAs which would be both potent to function in neurons, effect synaptic processes, and are circumstantially evident in epilepsy models in mice. From >1000 miRs in our analysis we zoned in on three miRs that satisfied these conditions (see elaboration below) and chose miR-211 for its unrecognized important "location" in the human genome (the epilepsy related 15q13.3 locus). We than found that it in-vitro targets the human UTR of nAChRα7—a gene in which a gain of function mutation results in nicotine-induced seizures. We then went to show predominantly, that miR-211 attenuates hyper-synchronization, non-convulsive seizure and susceptibility to convulsive seizures. Moreover to that, miR-211 reduction in the brain lead to cholinergic-receptor-genes and miR-134 expression changes regulation of and TGFbetaR-II pathway;

A yet additional functional similarity between the functional roles of miR-211 in mice and men was the link to memory and to Alzheimer's (AD) related pathology—human Brain samples from patients with AD showed miR-211 over-expression, as did an AD (APP-MyD88) model mice.

Our results and claimed invention pertain to interference with seizures and epilepsy via controlling for the levels of miR-211.

Specifically, and in detail: we identified miR-211 as a putative attenuator of cholinergic-mediated seizures by intersecting forebrain miR profiles that were Ago-precipitated, synaptic vesicle target-enriched or differentially expressed under pilocarpine-induced seizures, and validated TGFβR2 and the nicotinic anti-inflammatory acetylcholine receptor nAChRα7 as murine and human miR-211 targets, respectively. To explore the link between miR-211 and epilepsy, we engineered dTg-211 mice with doxycycline-suppressible forebrain overexpression of miR-211. These mice reacted to doxycycline exposure by spontaneous electrocorticography-documented non-convulsive seizures, accompanied by forebrain accumulation of the convulsive seizures-mediating miR-134. RNA-sequencing demonstrated in doxycycline-treated dTg-211 cortices over-representation of synaptic activity, Ca²⁺ transmembrane transport, TGFβR-II signaling and cholinergic synapse pathways. Of note: TGFβR-II signaling has been linked to lead to epileptogenic prone neuronal tissue in relation to cholinergic imbalances. Brain injury leads to the development of an epileptogenic prone neuronal tissue and recurrent epileptic seizures. Similarly following an acute status epilepticus (SE) event there is also development of hyper-excitability and recurrent seizures, and a therapeutic for these conditions is very much required. Additionally, a cholinergic dis-regulated mouse model over-expressing a miR-refractory acetylcholinesterase-R splice variant (Mishra, Friedson et al. 2017) showed a parallel propensity for convulsions, miR-211 decreases and miR-134 elevation, accompanied by deficient capacity for navigation learning which is reminiscent of that of Alzheimer's disease patients. Given the above findings, and since cholinergic signaling can block inflammation via nAChRα7 blockade of NFkB-induced production of cytokines, we further profiled both hippocampal miRs and coding mRNAs in in-house Alzheimer's model mice with mutated human amyloid plaques and ablated innate immunity due to MyD88 knockout (Goll, Bekenstein et al. 2014). Notably, miR-211 levels emerged as conspicuously hyper-expressed in these mice with shortened life expectancy (<5 months), with many of its coding targets suppressed, and with massive changes in neuronal signaling and cholinergic pathways.

We noted MiR-211 decline induces transcriptome changes of endothelial, synaptic and cholinergic functions. To explore the global transcriptional changes following miR-211 suppression, and test if they relate to specific brain cell types, we compared dTg-211 brains' transcripts to controls. Specifically, we tested highly expressed genes characteristic of neurons, astrocytes, oligodendrocytes and their progenitor cells (OPCs), microglia and endothelial cells (40) (FIG. 4A, B). None of the cell type marker groups showed changes in dTg-211 brains compared to controls. However, comparing dTg-211 transcripts in brains with and without Dox (FIG. 4C) demonstrated that 19 of 21 endothelial cell markers, but none of the other cell type markers showed an increase following Dox administration (P<0.05, perturbation analysis, see Methods). Thus, miR-211 reaction to Dox appeared to potentiate endothelial gene expression, predicting functional relevance for neurovascular unit activities. We also searched for Dox-induced changes in the expression of cholinergic receptor genes. The excitatory muscarinic ACh receptor-5 (mAChR5, 31), a positive effector of cholinergic synaptic transmission was elevated by 4-fold (FIG. 4D). Likewise, the excitatory nAChRα-1 neuronal nicotinic receptor and α-5 nicotinic receptor (Chrna5), the stress-inducible muscarinic m1 receptor and the ionotropic α-7 nicotinic receptor (Chrna7), responsible for post- and presynaptic excitation and blocker of inflammation, were all elevated. In contrast, the metabotropic muscarinic ACh receptors-4 and -2 (mAChR4, mAChR2) were both two-fold reduced following Dox administration (FIG. 4D, scheme in FIG. 4E). MAChR4 is located on both pre- and post-synaptic sites in brain cholinergic synapses, and exerts inhibitory effects on synaptic firing (44) with a role in locomotion. Additionally, we noted increases in butyrylcholinesterase (BChE, supplementary FIG. S4B), which hydrolyzes ACh in the brain alongside AChE and is elevated in AD brains. In contrast, we noted decrease of ATCAY/BNIP-H, an ataxia-related brain-specific scaffold protein, which was recently found to recruit Choline Acetyltransferase (ChAT) to neurite terminals, and promote cholinergic signaling (46, 47). Furthermore, within 4 days following Dox administration, dTg-211 mice presented 4-fold increases in the forebrain levels of miR-134 (FIG. 4F), known to be causally involved with the induction of convulsive seizures (10-12, 48). To examine how extra-synaptic cholinergic imbalance would affect miR-211 expression and the risk of epilepsy, we employed transgenic AChE-R (TgR) mice over-expressing the soluble, non-synaptic stress-induced splice variant of AChE from which the 3'-untranslated region (UTR) which contains the miR regulatory element (MRE) had been deleted (FIG. 4G, scheme). TgR mice, which constitutively overexpress AChE-R that catalyzes ACh breakdown in extra-synaptic sites and show chronic stress behaviors, are hyper-sensitized to nicotine administration (49). Intriguingly, these mice also experienced higher susceptibility to seizures, manifested as larger fraction of mice presenting full status epilepticus after pilocarpine injection (FIG. 4H). This was accompanied by shorter latency until status epilepticus was observed (FIG. 4I, P<0.05), reduced miR-211 expression in the hippocampus and frontal cortex compared to controls (FIG. 4J), and overexpression of miR-134 in the prefrontal cortex and hippocampus (FIG. 4K), possibly in relation to their hyper-synchronous state. Thus, modified cholinergic regulation in TgR mice elevated both forebrain miR-211 and miR-134 levels and exacerbated susceptibility to epileptic seizures. We noted that in EEG/ECoG measurements from mice, the slow hypersynchronous cortical activity is reminiscent and of several human syndromes manifesting with epilepsy. The recordings and expression data together with the genetic and transcriptional information indicates OR suggests that forebrain miR-211 maintaining OR elevating miR-211 levels in mice and men may be protective against spontaneous non-convulsive seizures, whereas its reduction may induce them.

In summary: We showed the putative role of miR-211 as a regulator of synaptic functions in the context of synchronous activity in human and mouse. The murine-related experiments are summarized below:

In a 1st mouse model, we explored this possible link between miR-211 and epilepsy by engineering Tg-mice with doxycycline-suppressible forebrain miR-211 overexpression. Doxycycline exposure generated spontaneous seizures, and RNA-sequencing demonstrated in doxycycline-treated dTg-211 cortices over-representation of pathways relating to synaptic activity, Ca2+ transmembrane transport, TGFβR-II signaling and cholinergic synapse pathways.

In a 2nd mouse model, we related these findings to another mouse model which over-expresses a miR-refractory acetylcholinesterase-R splice variant. Expression changes in miRs as well as phenotypical similarities concord with a cholinergic link.

In yet a 3rd mouse model, which relates to the immune deficiency in AD, miR-211 was very substantially changed. Importantly, we note transcriptional changes concordant with the results of the 1st mouse model.

In conclusion: this work has been based on a set of different transgenic model mice, human derived samples and cell cultures, all of which suggest that miR-expression dynamics plays a key role in hypersynchronous neuronal activity, relating to epilepsy and cholinergic brain signaling.

Taken together, our findings demonstrate that in mice, dynamic miR-211 decreases induce hyper-synchronization, and non-convulsive seizures, accompanied by expression changes in cholinergic and TGFβR2 pathways as well as in miR-134.

BRIEF DESCRIPTION OF THE DRAWINGS

The invention can be understood from these detailed results, but alternatively articulated as a description of the experimental results incorporated herein from U.S. Provisional Patent Application No. 62/640,139.

Result-set No 1: pertaining to identifying MiR-211 as a synaptic candidate associated with cholinergic signaling-induced seizures. (a) Three candidate miRs (miR-211, -218, 27a) emerged by intersecting rodent miRs whose levels modify following exposure to the cholinergic facilitator pilocarpine (145 miRs, 6); interact with the RISC complex protein Ago2 in CamKIIa-expressing cells (83 miRs, 26); and target synaptic vesicle transcripts (94 miRs, 80), predicting involvement in cholinergic-related epileptic seizures. (b) qRT-PCR-measurements show mmu-miR-211 decline in hippocampal RNA 24 hrs following exposure to pilocarpine. (c) Human MiR-211, as well as it's in silico target, nicotinic nAChRα7 and 5 other genes localize to a 15q13.3 chromosomal region where heterozygote deletions entail cognitive impairments with recurrent seizures. (d) The seed domain of hsa-miR-211-5p shows sequence complementarity with the inflammation regulating nicotinic nAChRα7. (e) Luciferase assay validated direct targeting by miR-211 of nAChRα7 in human embryonic kidney cells.

Result-set No 2: dTg-211 mice show spontaneous non-convulsive seizures following doxycycline-induced reduction of forebrain miR-211 excess. (a) DTg-211 mice carry the CamK2a promoter, followed by a trans-activator (tTa) coding sequence and a pTRE-transgene inducing Doxycycline-suppressible expression of mmu-miR-211 in forebrain neurons. (b) MiR-211 over-expression in the mouse forebrain but not cerebellum of is Dox-suppressible. Expression normalized to CamK controls. (c) Dox-suppressed miR-211 levels reach basal levels within days. (d) DTg-211 mice were administered Dox before and after birth, preventing transgene overexpression during development. ECoG recordings in dTg-211, but not control mice showed synchronous neuronal cortical activity after Dox-treatment, parallel to declined miR-211 levels. (e) DTg-211 mice presented ECoG-recorded seizures exclusively after Dox administration. (f) ECoG plots showing No. of seizures per day in single dTg-211 mice and controls (red, blue). Dashed gray line marks initiation of Dox administration. (g) Representative ECoG recording plot shows a seizure of a Dox-exposed dTg-211 mouse; corresponding heat-map shows representative higher power seizure of low frequency oscillations (~5 Hz) at the same time window. (h) Blow-up of a single event (marked by asterisk in d), presenting an enlarged section of the seizure activity, with spike and wave form.

Result-set No 3: Dox-treated dTg-211 mice show sustained susceptibility to PTZ-induced convulsions alongside TGFβR-associated gene changes in RNA seq. (a) Scheme of Pentylenetetrazol (PTZ) injection 4-days after 5-day Dox administration, to examine long-term susceptibility to this convulsant. See sup FIG. 3a for increased manual convulsions-index scores in dTg-211 mice. (b) ECoG recording shows larger spikes/min counts, reflecting seizure-susceptibility in PTZ-exposed dTg-211 mice compared to CamK controls; (c) Number of seizures; (d) Latency to 1st spike; (e) Number of seizure-events by Neuronal-networks analysis; and (f) Latency to first seizure. (g) DTg-211 mice regained miR-211 overexpression after Dox removal, at time of PTZ test. (h) Luciferase validation tests of miR-211 targeting of the murine TGFβR-II 3'-UTR but not a control sequence. (i) Reduced TGFβR-II protein concentration (two fold) in dTg-211 frontal cortex (ELISA, n=7+7, p<0.001). (j) Increased TGFβR-II mRNA levels following Dox administration. (k) Fold-change volcano plot differences for dTg-211 with/without Dox (right pane) compared to dTg-211/ CamK brains (left pane). Dots represent genes, with positive or negative 2-fold change (orange), passing cutoff threshold for significance (red), both (green) or unmodified (black). (1) Empirical Cumulative Distribution Function (ECDF) plots show differential expression (p-values) following Dox, of reduced (orange) but not elevated genes (green) in dTg-211 cortices or in all genes (gray). (m) Cortical genes up-regulated in dTg-211 are reduced (red) following Dox compared to (n) all genes. (o) Per-gene fold-changes following Dox for TGFβ-signaling genes modified 12 hrs. following status epilepticus. (39)

Result-set No 4: MiR-suppression in dTg-211 mice alters cell marker genes and cholinergic receptors, and cholinergic mouse model show concordant miR-changes alongside increased seizure susceptibility. (a) Experimental setup: CamK:Tta mice bred with Tg-pTRE-211 mice generated dTg-211 mice and littermate CamK-controls. Illumina-compatible libraries from Frontal cortex-RNA of mice before or under doxycycline (color-coded squares) were sequenced. (b) Sustained cell-type marker (40) in dTg brains; (c) Elevated endothelial marker genes following Dox. (d) Modified muscarinic (M) and nicotinic (N) cholinergic receptors in Dox-treated dTg-211 brains. (e) Scheme of cholinergic receptors and regulators (shown in d) in brain cholinergic synapses. Note Dox-induced downregulation of cholinergic receptors suppressing synaptic transmission: CHRM2 and CHRM4 (M2 and M4); and upregulation of facilitators CHRM5 (M5), CHRNA5 and CHRNA7 (α5 and α7). MiR-134 upregulation in dTg-211 mice following Dox administration parallels the timeframe of seizure induction in this model. (g) Scheme of the synaptic and non-synaptic AChE transcript variants, and corresponding protein forms. (h) Mice overexpressing the non-synaptic cholinergic enzyme AChE-R (TgR(81)) show higher propensity with (i) shorter latency for status epilepticus event following Pilocarpine injection, alongside (j) miR-211 reduction and (k) miR-134 elevation in pre-frontal cortex (PFC) and hippocampus (Hipp) of TgR mice.

Result-set No 5: Protein-protein interaction network of Dox-induced differentially expressed synaptic vesicle and cholinergic genes. (a) Protein-protein interaction-based interconnected network of stringently-defined 134 differentially expressed node genes and overall 427 genes. (b) Fold changes ±SEM of the synaptic vesicle cycle pathway genes within the network. (c) Fold changes ±SEM of the cholinergic synapse genes within the network. (d-e) Enriched biological process GO-terms for PPI-networks for genes differentially expressed following Dox, either down or up. (Fold enrichment, stars denote significance p-value based on permutation analysis). Result-set No 6: Mmu-miR-211 expressing mice show reduced memory abilities in the Morris Water Maze, and hsa-miR-211 is overexpressed in AD patient brains. (a) PANTHER classification of gene ontology shows Dox-induced enrichment of differentially expressed gene groups, mainly regulation (Reg.) of neuron-related pathways in the dTg-211 brain transcripts (Asterisk, see methods). (b) Time to reach platform in the MWM shows reduced learning ability in the 1st and 2nd training days for dTg-211 mice. (c) Search strategy scores divided by trials and days for individual dTg-211 and CamK mice. Fewer trials of dTg-211 mice in the last days showed focal or directed strategy. (c) Loss of preference of the platform quadrant, reflecting impaired reference memory for dTg-211 compared to CamK mice in probe trials. (e) Higher miR-211 levels (~2-fold) in post-mortem Alzheimer's entorhinal cortices (72) compared to non-demented controls, n=7 each, p<0.05, Student's t-test.

Result-set No 7: Scheme depicting the cross of transgenic lines (MyD88$^{-/-}$ with B6C3-Tg:APPswe, PSEN1dE9) all from a C57BL6 background to generate MyD88$^{-/-}$-APP$_{sw}$/PS1ΔE9 mice. As the cholinergic system and Alzheimer's disease (AD)-related pathologies are long known to be interconnected; AD entails memory loss and has long been observed to entail perturbed cholinergic signaling and loss of brain cholinergic cells (ref: Davies and Maloney 1976). To peer into the possibility that miR regulation, and specifically that of miR-211 may have a role in the context of AD and its cholinergic disruption, we utilized samples from triple transgenic model mice carrying a mutated human amyloid precursor protein APP gene, a mutated presenilin 1 PS1 gene and an ablated innate immune system via knockout of the Toll-Like Receptor (TLR)-related innate immune mediator: The Myeloid Differentiation Primary Response 88 MyD88 gene (ref). The cumulative augmentation of these transgenic manipulations served us in modeling the contribution of AD-related Aβ pathology in the absence of an intact innate immune signaling system. Small RNA sequencing from these mice noted numerous differentially expressed miRs in the triple transgenic hippocampi. Of note, alongside Let7-k and miR-1264, miR-211 was conspicuously upregulated in the hippocampi of these mice by an order of magnitude. Also, miR-200-a, 3068 and 344-b were all higher in MyD88 null mice than in triple transgenic mice. These mice, expressing mutant forms of PSN1, APP and MyD88, can serve to reflect the functional role of the innate immune system in AD. An important phenotype we noted is the reduced lifespan and abrupt death of these triple transgenic mice in early adulthood (Goll, Bekenstein et al. 2014). After 250 days (8 Mo.) triple transgenic mice were twice as likely to die as controls, with death rate peeking in 4 months of age.

Result-set No 8: AD-innate-immune model mice show reduced lifespan with exacerbated death starting at young adulthood. Kaplan-Meier survival curves showing the cumulative survival probabilities in MyD88-/- (n=47), APP/PS1 MyD88+/- (n=45) and APP/PS1 MyD88-/- (n=41) over 10 months (log-rank test p<0.001).

Result-set No 9: PCA of miR expression in MyD88 null mice shows separation between control (black triangles) and APP-PS1. And A per-miR coefficient of variance shows higher inter-group variance for many of the expressed miRs than expected by chance, across expression levels (CPM). Concordantly, we examined the transcriptional expression profile of both miRs and mRNAs and the interactions between them in the hippocampus of these triple mice. Expression of miRs was different between MyD88-/- mice transgenic for APP-PS1 and control MyD88-/-, as evident from principal component analysis (PCA) for miR-expression and analysis of variance.

Result-set No 10: MyD88-AD mice show both elevation and downregulation in MyD88-AD mice. For addressing this question specifically in the cholinergic context, we examined the expression of cholinergic receptors. Intriguingly, cholinergic Muscarinic Receptors 1, 3 and 4 (CHRM1, CHRM3, CHRM4) showed elevation in MyD-APP mice V.s. MyD88-/- controls; while Cholinergic Muscarinic Receptor 5 (CHRM5) showed reduction. The relation of these changes to those observed in dTg-211 mice under the Dox- is of interest, but will not be elaborated upon. Result-set No 11: Modifications of miR-211 target genes: MyD88-AD mice show both elevation and downregulation of expression in the hippocampus of MyD88-AD mice in respect to MyD88-/- controls. We also observed specific targets of miR-211 to be modified in the MyD-AD hippocampus (FIG. 7 K). These include Zinc Finger and BTB Domain Containing 7C (ZBTB7C), which is upregulated in endothelial cells in both in-vitro and in-vivo models of ischemia and that was (together with ANGPT1) implicated in the Susceptibility to undergo ischemic injury in response to cerebral ischemia (Du, Zhou et al. 2015). Of note, dTg-211 mice following Dox likewise showed a two-fold reduction in ZBTB7C in respect to both control or no-Dox dTg-211 mice; Ribosomal Protein S6 Kinase A3 (RPS6KA3) whose impairment causes a non-syndromic form of mild to moderate mental retardation (Merienne, Jacquot et al. 1999, Field, Tarpey et al. 2006) was also modified. Other changes were noted in the schizophrenia related Plexin A2 (PLXNA2, Mah, Nelson et al. 2006) and in the Iron Responsive Element Binding Protein 2 (IREB2) to which allelic association was suggested for AD (Coon, Siegel et al. 2006).

Embodiments for the Invention

Embodiments for the invention comprise inter-related experimental model systems and methods for limiting or enhancing the chance for seizures in the mammalian brain.

In some embodiments model mice expressing oligonucleotides substantially similar to miR-211 or complements thereof—provide insight into the epileptic state or provide a backdrop for discovery of additional agents for therapeutic use. Methods for limiting or enhancing the chance for seizures in the mammalian brain by introducing oligonucleotides provide transgenic or viral expression or delivery by yet additional means to the brain of oligonucleotides to control and limit reduction in the abundance of miR-211.

Definitions of Terms

In the present invention, the term "seizure" should be understood as uncontrolled electrical activity in the brain, which may produce a physical convulsion, minor physical signs, thought disturbances, or a combination of symptoms. The type of symptoms and seizures depend on where the abnormal electrical activity takes place in the brain, what its cause is, and such factors as the patient's age and general state of health. Seizures by this definition can be caused by head injuries, brain tumors, lead poisoning, mal-development of the brain, genetic and infectious illnesses, and fevers. Yet in as much as half of the patients with seizures, no direct cause can yet be found.

In the present invention, the term "seizure-related disorder" or "seizure related condition"-should be understood to mean: both conditions involving tonic-clonic (grand-mal) seizures and petit mal seizures—these together include brain injury stroke, CNS infection-associated seizures, brain tumors, traumatic brain injury, neurodegenerative disorders, and metabolic disorders which are known to cause seizures.

In the present invention, the term "epilepsy" pertains to a central nervous system (neurological) disorder essentially in humans which brain activity becomes abnormal, causing seizures or periods of unusual behavior, sensations, and sometimes loss of awareness. Brain activity phenomena in other mammals may be described as "epileptic" as per some similarities in recordings in brain activity.

In the present invention, the term "Intractable epilepsy" pertains to a seizure disorder in which a patient's seizures fail to come under control with treatment. These seizures are sometimes also called "uncontrolled" or "refractory."

In the present invention, when addressing "expression" as "in the brain" it refers to an expression that is unique and essentially undetectable outside of the Brain of an animal or human subject.

In the present invention, the term when addressing "expression" as "predominantly in the brain" it refers to an expression in which the fold-increase detectable in the brain of the said animal or human subject is substantially higher than over the fold-increase detectable in any other tissue to be examined out of the brain. Wherein the "substantially higher" old increase is: fourfold, tenfold, twentyfold or one hundred-fold over the fold increase in other tissues examined.

In the present invention the term "oligonucleotides" pertains to short nucleic acid polymers such as RNA, DNA and backbone-modified or otherwise modified versions used and known in the ART: oligonucleotides can be expressed in vivo or in vitro or alternatively generated by man-designed chemical reactions such as by Solid-phase synthesis. Chemically the oligonucleotides molecules described herein may be for example, locked nucleic acid (LNA), RNA, DNA, 2-O-methyl-blocked, morpholino or phosphorothioate oligonucleotides. These may take the form of short, (single- or double-stranded) DNA or RNA molecules, and "oligonucleotides" is construed to include antisense oligonucleotides (ASO), RNA interference (RNAi), and aptamer RNAs. An oligo may be considered as substantially similar if it holds 90%, 93%, 95%, 97%, 99% or 100% similarity to a said sequence. Functionally a person in the ART of miRNA will most commonly consider of a said sequence to be substantially similar to a (mature) miRNA if it shares 95% similarity or 100% similarity allowing (or not) for a single mismatch along the ~20 bp alignment.

In the present invention and as common in the art of cell biology microRNAs (miRNAs, miRs) are short non-coding RNAs (ncRNAs) that regulate gene expression at the level of translation, having features known in the ART.

Locked nucleic acid (LNA) are modified RNA nucleotide in which the ribose moiety is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired and hybridize with DNA or RNA according to Watson-Crick base-pairing rules.

An LNA mimetic OR inhibitor a shorter than 20 bp of base-paring may functional due to the strong binding of this nucleic acid species to RNA, and as is known in the ART. LNAs are a preferred embodiment for administration in the present invention, such as for mimetic or as an antagomiR, and by diverse means of delivery as will be specified and as is known in the ART.

Phosphorothioate are RNA-like nucleic acids with internucleotide linkages are resistant to nucleases, phosphorothioate oligonucleotides are also relatively compatible for use in vivo, since they are may pass more readily to the interior of the cell via the plasma membrane, when used as antisense, phosphorothioate may be used to downregulate gene expression by hybridizing to a target mRNA, or pre-miR. To resist exonucleases, the oligonucleotide would preferably have phosphorothioate linkages near both the 5' and 3' ends; and as is known in the ART.

Morpholino oligomers (A.K.A. phosphorodiamidate Morpholino oligomer; PMO), has DNA bases attached to a backbone of methyl-enemorpholine rings linked through phosphorodiamidate groups. Morpholinos are classically used to block access to RNAs such as for knocking down gene function or inhibiting miRs.

2'-O-methyl-modified phosphorothioate antisense oligonucleotides (2-O-methyl-blocked; 2'OMe) is a naturally occurring post-transcriptional modification of RNA, such as in tRNAs Oligonucleotides synthesized to contain 2'OMe have increased Tm for RNA duplexes, and the oligo is protected from single-stranded endonucleases.

More globally, in the present invention miRs can be modified in accordance with the invention using any suitable chemical moiety including, for example, also boranophosphate, 2'-fluoro, PEG, terminal inverted-dT base, 2'-fluoro N3-P5'-phosphoramidites, or combinations thereof. In particular preferred embodiment, the miR is modified to include LNA (see also Grunweller, et al. (2003) NAR 31:3185-93).

All of the oligonucleotides described herein for administration of a synthesized molecule may be provided be the diverse means known in the ART for experimental and medicinal use.

Specifically, delivery to the brain of a subject or model organism may be done by injection to the brain OR by systemic injection specifically in conditions in which blood barrier is interrupted. Encapsulation of the oligonucleotides in liposomes or alongside nanoparticles and as previously shown and known in the ART.

In the present invention an inducer of a molecular expression system is a small molecule functional in modifying that system; and such as doxycycline (Dox), and as is known in the ART.

In the present invention doxycycline (dox) is a derivative of tetracycline, a preferred effector for tetracycline transregulation and as is known in the ART of transgenic systems.

Tet-Off expression system, comprises a tetracycline-controlled transactivator protein (tTA) which is composed of the Tet repressor DNA binding protein (TetR) fused to a VP16 activator from Herpes Virus, regulating the tetracycline-responsive promoter element (TRE; and in our case the miR-211). In the absence of Tc or Dox, tTA binds to the TRE and activates transcription of the target gene. In the presence of Tc or Dox, tTA cannot bind to the TRE, and expression from the target gene remains inactive.

In the present invention administering is construed as providing a substance such as by adding it to food or injecting an organism or patient.

An externally synthesized oligonucleotide is any oligonucleotide molecule not synthesized in-vivo per a subject or animal.

In the present invention as used herein interchangeably, a "miRNA gene product," "microRNA," "miR," or "miRNA" may, by context, refer to the unprocessed or processed RNA transcript from a miRNA gene, and as indicated by the context. As the miRNA gene products are not translated into protein, the term "miRNA gene products" does not include proteins—the term "miR-211" should be understood to mean the mammalian-conserved intragenic (intronic) miR. Of note: during miRNA biogenesis a pri-miRNA transcript is transcribed—this form is cleaved to generate the pre-miRNA. A 70-100 bp form which is found in a stem and loop form.

As common in the ART, we and others have cloned a miR sequence to express in a transgenic manner in the form of the pre-miR. This is preferable for practical reasons. We acknowledge that the expressed for also leads to and generates some levels of the "star" form of the miR—that is the complementary portion of the mature miR which may assume a function, as well as the loop portion—which is detectable in sequencing. When In the present invention, the term "miR-211" is used it concerns the functional miR-211-5p, which has been shown to be the prominent form and assumes the function of the 'gene' and expressed pre-miR is derived from the prominent form (mmu-miR-211-5p, SEQ ID No. 1, alternatively hsa-miR-211-5p, SEQ ID No. 2) rather than the pre-miR or the star form (mmu-pre-miR-211/mmu-miR-211-3p, SEQ ID No. 3/SEQ ID No. 5 alternatively, in humans: hsa-pre-miR-211/hsa-miR-211-3p, SEQ ID No. 4/SEQ ID No. 6). When the term "miR-211" is used in the context of a transgene expressed—it concerns the pre-miR form (such as mmu-pre-miR-211 or hsa-pre-miR-211). When describing inserting/injecting/administering a synthesized molecule to a mammal—the term "miR-211" by default concerns the functional mature mmu-miR-211-5p/hsa-miR-211-5p, and unless otherwise noted. We find this wording definite; and to substantial extent is commonly used by persons in the ART.

Of note: The miRs of the invention and their explicit sequences thereof are well-known in the art and can be found in the miRBase Sequence Database and Registry (Kozomara & Griffiths-Jones (2011) Nucl. Acids Res. 39:D152-7; Griffiths-Jones, et al. (2008) Nucl. Acids Res. 36:D154-8; and Griffiths-Jones (2004) Nucl. Acids Res. 32:D109-111.

In the present invention, the term "reduction" or "decrease" or "inhibiting expression" should be understood as the reduction in the relative number of miR molecules (as per a so-called 'constant' or housekeeping molecule constituting a reference)—and as is normally addressed in the art by quantitative PCR (qPCR) or by high throughput sequencing.

In the present invention "mimetic" molecules (or oligo-mimetics) are chemically modified compounds designed to mimic the action of naturally occurring molecules; but with alternative chemistries to the nucleic acid bases.

The term "inhibition of miR-211 activity" should be understood as including direct inhibition such as by a molecule which binds to the miR and directly inhibits its activity (examples include binding partner, an interfering oligonucleotides molecules, as described above, and such as, for example, LNA, RNA or phosphorothioate oligonucleotides.

Of note: agents suitable for interference of cellular RNAs include antago-miRs, antisense molecules, small hairpin RNA molecules (shRNA), small interfering RNA (siRNA) molecules, microRNA "sponges", decoy oligonucleotides and aptamers.

Small hairpin RNA (shRNA) molecules are short RNA molecules having a small hairpin loop in their tertiary structure that may be employed to silence genes. The design of shRNA molecules capable of inhibiting miR-211 by binding preferably onto the pre-miR are apparent to those skilled in the field of shRNA design.

In the present invention, the term "antagomir" should be understood to mean a class of chemically engineered oligo-nucleotides used to silence endogenous miRs by base paring with them. More explicitly, an antagomir is a small synthetic oligo that is complementary to the specific miR target portion such as to inhibit Ago2 cleavage of the target by the miR.

Sponge RNAs are small synthetic RNAs that are introduced to the cell and function like antagomirs yet bind more than one miR.

As used herein, "treating" or "treatment" of a disease or disorder refers to arresting, reducing, ameliorating or delaying the onset of a disease, disorder, or at least one clinical symptom or physical parameter of a disease or disorder, which may or may not be discernible by the patient. In certain embodiments, "treating" or "treatment" refers to inhibiting or controlling the disease or disorder, either physically (e.g., stabilization of a discernible symptom), physiologically (e.g., stabilization of a physical parameter), or both. As used herein, an "effective amount" of a miR gene product is an amount sufficient to measurably restore the self-evident physiological state. Alternatively stated, an effective amount of a miRNA gene product measurably restores, reverses or stabilizes neural function to the EEG measured brain activity expected from an intact subject or animal and in concordance to the practice and the medical ART. Arguably, one skilled in the art can determine an effective amount of a miRNA gene product to be administered to a given subject, by taking into account factors, such as the size and weight of the subject; health and sex of the subject; the route of administration based on previous publications in the field; and whether the nature of administration: E.g. regional or systemic. In addition, one skilled in the art can determine an appropriate dosage regimen for the administration of an isolated miRNA gene product to a given subject. For example, a miRNA gene product can be administered to the subject once (e.g., as a single injection or deposition). Alternatively, a miRNA gene product can be administered multiple times to a subject. Where a dosage regimen includes multiple administrations, it is understood that the effective amount of the miRNA gene product administered to the subject can include the total amount of gene product administered over the entire dosage regimen In the present invention and as known in the ART various delivery systems can be used to administer a synthetic oligo for therapeutic use—by different routes these can include intra-nasally intradermal, intramuscular, intraperitoneal, intravenous, subcutaneous, intranasal, epidural, intranasal, intracerebral, and oral routes. Specifically, this invention is concerned delivery to the CNS of a mammal—specifically a human, and also to a model organism such as a rat, mouse OR non-human primate. Delivery means can thus include injection to brain cavity, using mini-osmotic pump, as known in the ART, as well as systemic administration—Intravenous delivery, oral delivery, intramuscular delivery, intrathecal delivery, and inhaled delivery. Appropriate methods for achieving these means of delivery are known to those skilled in the art of drug delivery.

A genetically modified animal is construed as meaning a transgenic OR a Genome edited animal, such as by CRISPR-Cas systems.

In some embodiments, the miRNA gene product is isolated. As used herein, an "isolated" miRNA gene product is one that is synthesized, or altered or removed from the natural state through human intervention. For example, a synthetic miRNA gene product, or a miRNA gene product partially or completely separated from the coexisting materials of its natural state, is considered to be "isolated." An isolated miRNA gene product can exist in a substantially-purified form, or can exist in a cell into which the miRNA gene product has been delivered. Thus, a miRNA gene product that is deliberately delivered to, or expressed in, a cell is considered an "isolated" miRNA gene product. A miRNA gene product produced inside a cell from a miRNA precursor molecule is also considered to be an "isolated" molecule.

Isolated miRNA gene products can be obtained using a number of standard techniques. For example, the miRNA gene products can be chemically synthesized or recombinantly produced using methods known in the art. Commercial suppliers of synthetic RNA molecules or synthesis reagents include, e.g., Dharmacon Research (Lafayette, Colo.), Pierce Chemical (part of Perbio Science, Rockford, Ill.), Glen Research (Sterling, Va.), and Cruachem (Glasgow, UK).

Alternatively, the miRNA gene products can be expressed from recombinant vectors, either individually or from the same or different vector. Recombinant vectors include circular or linear DNA plasmids and typically contain a suitable promoter. Suitable promoters for expressing RNA from a plasmid include, e.g., the U6 or Hi RNA pol III promoter sequences, or the cytomegalovirus promoters. Selection of other suitable promoters is within the skill in the art. The recombinant plasmids of the invention can also include inducible promoters for expression of the miRNA gene products in brain cells. The miRNA gene products can also be expressed from recombinant viral vectors. The RNA expressed from the recombinant viral vectors can either be isolated from cultured cell expression systems by standard techniques, or can be expressed directly in brain cells.

In the present invention, "seizure-generating-stimuli" relates to the fact that some seizures such as focal seizures or seizures generated in a certain region of the brain, may be initiated in the following pathological causes (ranging from substance abuse to rhythmic flashing lights) and propagated throughout the brain. Moreover, stimulation of the brain in a model organism by stimulant substances has long been used to seizures, epileptic events and induce epileptogenesis.

Unless otherwise indicated, all numbers defined above, used in this specification are to be understood as being modified in all instances by the term "about". Accordingly, unless indicated to the contrary, the numerical parameters set forth in this specification are approximations that may vary by up to plus or minus 10% depending upon the desired properties to be obtained by the present invention.

Units, prefixes and symbols may be denoted in their SI accepted form. Unless otherwise indicated, nucleic acids are written left to right in 5' to 3' orientation; amino acid sequences are written left to right in amino to carboxy-orientation, respectively. Numeric ranges are inclusive of the numbers defining the range.

The invention will now be illustrated by the following non-limiting Examples.

EXAMPLES

Materials and Methods

Transgenic Mice Generation and Experiments

We generated pTRE-miR-211 mice by cloning the pre-mmu-miR-211 sequence into a pTRE-tight vector, followed by pronuclear injection at The Weizmann Institute of Science Animals Facility. Mice were held in SPF conditions at The Hebrew University—an AAALAC International accredited institute. All procedures, including animal tests were approved by the institutional ethics committee (Ethics No: NS-16-14729-4), with concordance to AAALAC International guidelines. Tta-CamKa Strain (CamK, Calcium/Calmodulin Dependent Protein Kinase II Alpha) was acquired, backcrossed and crossed and housed as in Supplementary Methods. DTg mice and CamK littermates were housed together and administered doxycycline (Dox) in parallel. The cholinergic muscarinic agonist pilocarpine (Sigma, Israel; 290-340 mg/kg) was intraperitoneally (i.p.) injected to mice as in (72).

For genotyping, Tail-tip PCR was used (sequences given in Supplementary Table S1). B6; CBA-Tg(Camk2a-tTA) 1Mmaya (CamK mice) were purchased from Jackson Laboratory, Farmington (Jax® Bar Harbor, Me.). Mice were backcrossed to FVB/N background for three generations and further crossed to generate double transgenic mice and littermate controls.

Behavioral Tests

Morris Water Maze (MWM):

Mice were subjected to a Morris water maze (as in Vorhees and Williams 2006) to assess learning and memory. Briefly, mice were released to search for a submerged platform in a fiberglass water tank, 1.2 m in diameter. Water temperature was fixed; and colored white for opaqueness. Lighting remained fixed, platform directions were queued with visible marks to allow for allocentric navigation, and

| | Sequence ID | Sequence full name | miRbase ID/ other database | Sequence |
|---|---|---|---|---|
| 1 | SEQ ID No. 1 | mmu-miR-211-5p | MIMAT0000668 | UUCCCUUUGUCAUCCUUUGCCU |
| 2 | SEQ ID No. 2 | hsa-miR-211-5p | MIMAT0000268 | UUCCCUUUGUCAUCCUUCGCCU |
| 3 | SEQ ID No. 3 | mmu-pre-miR-211 | MI0000708 | CUGCUUGGACCUGUGACCUGUG GGCUUCCCUUUGUCAUCCUUUGC CUAGGCCUCUGAGUGAGGCAAG GACAGCAAAGGGGGCUCAGUG GUCACCUCUACUGCAGA |
| 4 | SEQ ID No.4 | hsa-pre-miR-211 | MI0000287 | UCACCUGGCCAUGUGACUUGUG GGCUUCCCUUUGUCAUCCUUCGC CUAGGGCUCUGAGCAGGGCAGG GACAGCAAAGGGGUGCUCAGUU GUCACUUCCCACAGCACGGAG |
| 5 | SEQ ID No. 5 | mmu-miR-211-3p | MIMAT0017059 | GCAAGGACAGCAAAGGGGGC |
| 6 | SEQ ID No. 6 | hsa-miR-211-3p | MIMAT0022694 | GCAGGGACAGCAAAGGGGUGC | systematic release directions were as in (Vorhees and Williams 2006). Each mouse was tested in four trials a day for 4 days, followed by a single day of probe trial, in which mice search for the platform which had been removed. Experiments were performed blind, using alias numbers per mouse, recorded from a monochromatic ceiling-fixed video camera and automatic movement tracing and quantitative data analysis was performed using EthoVision® XT (Noldus version 8, Information Technology b.v., Wageningen, The Netherlands; Noldus, Spink et al. 2001)

Luciferase Assay

MiR-211-5p direct targeting was predicted in-silico and experimentally assessed using in vitro Luciferase measurement with the Dual-Luciferase kit (Promega, Madison, Wis.), 48 h after transfection. Specifically, a 3' untranslated region (3'-UTR) fragment of human nAChRα7 OR murine TGFβR-II transcripts (both similar in mouse and human), was cloned into a luciferase reporter vector. Reporter and miR-211 expression vector (Genecopia, MmiR3291-MR04) were transfected into HEK293-T cells (ATCC, Manassas, Va.) using polyethylenimine, and luciferase activity measured and normalized according to manufacturer's instructions.

ELISA

Mice frontal cortices were homogenized in RIPA buffer containing protease inhibitor (1:200) and centrifuged. Sample protein content was measured with the Lowry assay (Thermo Scientific, France). Samples were further diluted 1:3 in PBS and used for quantifying TGFbR2 by EIAab kit (Cat.: E9935m) as per manufacturer's instructions.

ECOG Recordings and Analysis

Electrocorticography (ECoG) recordings were performed as previously described (73). Briefly, under deep isoflurane anesthesia (1-3%) mice were placed in a stereotaxic frame. After shaving and disinfecting the dorsal aspect of the head, the skull was exposed by a longitudinal incision. Holes were drilled in coordinates 3 mm caudal and 2 mm lateral relative to bregma. Stainless steel screws were fixed to the holes. After placing a wireless transmitter (Data Science International, St. Paul, Minn.) with in a pocket formed subcutaneously in the dorsal aspect of the body, the electrodes were connected to the screws and isolated with bone cement. Before termination of anesthesia, buprenorphine was administered (i.p., 0.05 mg/kg). Following recovery, animals were moved to a behavior room with 12 hr light/dark cycle and had access to food and water ad libitum. After 4 days of habituation we began continuous ECoG recording, using a home-made MatLab-based program that allows reliable unbiased detection of seizures (Bar-Klein et al. 2014). The results were revised manually and blindly. ECoG spikes were implemented via the wavelet transform (WT) algorithm (74) following a band-pass filtration of the ECoG signal between 1-45 Hz. After automated detection and clustering using the MatLab program, blind human revision was performed to reassure the results.

Pentylenetetrazol-Induced Seizures

Animals were placed individually in Plexiglas boxes and seizure behavior was observed for 30 min following PTZ injection (50 mg/kg, s.c.). Seizures intensity was evaluated (as in 75). Parallel ECoG recording was analyzed as mentioned above.

RNA Samples Collection for RT-qPCR and Sequencing-Compatible Libraries

Mice were anesthetized with isoflurane prior to cervical dislocation and their brain regions including frontal cortices were dissected and collected in liquid nitrogen. For RNA-sequencing, RNA was extracted by miRNeasy kit (QIAGEN), RNA quality determined with 6000-Nano Bioanalyzer (Agilent, Santa Clara, Calif.), and samples with RIN values ranged between 8 and 8.9 were used. RNA was extracted for qRT-PCR validation analysis using TRIzol® Reagent (Invitrogen), as reported (see 76). cDNA and PCR as are in supplementary methods.

High Throuphput RNA Sequencing

Sequencing-compatible poly A-terminated single-end libraries were generated using an RNA Library prep kit (NEBNext® Multiplex, E7330S, New England Biolabs) following manufacturer's instructions, with 12 amplification rounds. Libraries were barcoded and sequenced on a NextSeq Series Sequencing System (The HUJ Center for Genomic Technologies) using two Illumina chips (Illumina 500® NextSeq High Output v2 Kit, FC-404-2005, Illumina). Raw cluster densities for samples ranged between 170-189 K/mm2. Reads were aligned (90% mapping) to the mouse transcriptome (TopHat2, 77), and expression analysis was performed using the DeSeq (78) software via R platform (79). Libraries from all tissues were overall similar in depth, with a similar distribution of transcript numbers per expression level and tag-wise normalized variance predictably correlated to expression levels (Supplementary FIG. S2A, B, C). A 6.2 log-CPM value for PPI thresholding represents upper 10 percentiles of 18,570 genes in data.

Bioinformatics, Pathway Analysis and Luciferase Assays

Cell type marker genes (from 40) were selected as mouse orthologues name-wise and their levels plotted as fold change, p-value presented after Bonferroni correction and permutation analysis used to determine significance per marker. Empirical Cumulative Distribution Function (ECDF) plots were generated in R via the stats package (79) after thresholding genes by counts (mean log(CPM)>1) and sub-setting by significance of differential expression. PANTHER (Protein ANalysis THrough Evolutionary Relationships; 51) version 10, Gene Ontology version: 1.2, annotated 22 Jun. 2016, was used for Gene Ontology (GO) of differentially expressed genes, for KEGG database (Kyoto Encyclopedia of Genes and Genomes). See Supplementary methods for details on luciferase assays and statistics analyses.

Human Derived Samples

Postmortem samples of entorhinal cortex from AD and age-matched controls were obtained from The Netherlands Brain Bank (NBB) at the Netherlands Institute for Neuroscience, Amsterdam (as in 72). Samples were collected following a written informed consent for a brain autopsy by the NBB.

qPCR

A qScript Kit (Quanta) was used for Reverse transcription. Real-time-PCR performed on a CFX-96 machine (Bio-Rad), and quantification performed using the ΔΔCt method, with snoRD47 as a loading control for miRs and β-actin for long transcripts.

Statistical Analyses

Differential expression in sequencing experiments was derived from adjusted p values in DeSeq (78) on R platform, after false discovery rate (FDR) correction. For specific genes presented, fold change and ratio values are shown as mean±SEM. For cholinergic receptors, t-test was used on normalized count data. For enrichment of cell type marker genes, p-value was defined based on permutation analysis. Box and whisker plots show 2nd and 3rd quintiles for box, and 1.5 quantile distances from median for whiskers, as by convention. Results were considered significant if P<0.05, P<0.01, P<0.001 (one, two or three asterisks), after correction for multiple testing when applicable. For ECoG seizure and spike observations, Mann Whitney test was used.

EXAMPLES

Example 1 intersecting publically available data to designate candidate miRs to be used in the attenuation of seizure phenotypes OR to model seizures: Publically available datasets are deposited in databases such as GEO. To indicate transcripts, and specifically, miRNAs which are potent OR may be potent to attenuate OR model seizures (such as for epilepsy) transcriptional features from publically available datasets was intersected in a specific manner: namely, to perform a non-biased search for neuronal miRs regulating synaptic processes and responding to cholinergic seizure-related cues, we intersected publicly available transcriptional profiles of miRs regulating synaptic vesicle transcripts, transcripts overrepresented in healthy forebrain immune precipitates of neuronal Argonaut 2 (AGO-IP) and differentially expressed following pilocarpine injection.

Three candidate miRs emerged: miR-211, miR-218 and miR-27a. Intersecting these groups, may also be viewed as representing predicting involvement in cholinergic-related epileptic seizures as they include (1) rodent miRs whose levels modify following exposure to the cholinergic facilitator pilocarpine (145 miRs); interact with the RISC complex protein Ago2 in CamKIIa-expressing cells (83 miRs); and target synaptic vesicle transcripts (94 miRs).

Example 2

Pilocarpine model mice show prolonged changes in miR-211 flowing exposure. Pilocarpine model mice are considered a classic experimental model for examining seizures, specifically of temporal lobe epilepsy seizures, and have been addressed also in the ART in the context of the 'transcriptional landscape' of gene expression. In is considered established in the ART that this cholinergic muscarinic receptor agonist pilocarpine when injected induces Status epilepticus (SE) which is followed by its neuropathological features, such as neuronal death, reactive gliosis, and remodeling of synaptic circuitry. We noted by qRT-PCR-measurements that mmu-miR-211 is reduced in hippocampal RNA 24 hrs following exposure to pilocarpine. Brain derived samples from pilocarpine mice samples were assayed for expression levels using qPCR after reverse transcription, as is common in the ART, and the expression of miR-211-5p in pilocarpine Vs controls samples was reduced post injection.

Example 3

Human MiR-211, as well as it's in silico target, nicotinic nAChRα7 and 5 other genes localize to a 15q13.3 chromosomal region where heterozygote deletions entail cognitive impairments with recurrent seizures. We noted that miR-211 (conserved in mammals in being an intragenic miR) is located within the TRPM1 calcium channel gene, itself within the 15q13.3 locus where heterozygote microdeletions (OMIM #612001) associate with mental retardation and recurrent epileptic seizures. We note that homozygous deletions associate with severe neurodevelopmental problems including epileptic encephalopathy. We also observed that in proximity to the TRPM1 gene and within the 15q13.3 locus is the nicotinic receptor nAChRα7 a gain of function mutation in which results in nicotine-induced seizures. Which was the bases for further experiments.

Example 4 miR-target interaction analysis finds human miR-211 to target the nicotinic receptor nAChRα7 in human-derived cells: we followed up an in-silico interaction analysis, which we performed and predicted the nAChRα7 to be a miR-targets for human (has)-miR-211 targets via a 7-mer miR response element (MRE), we performed an experimental assay/validation:

human miR-211 was expressed from an expression vector in cultured human derived cells: namely HEK293 (human embryonic kidney) cells and directly downregulated a luciferase expression construct containing the nAChRα7 3' UTR, further supporting both the cholinergic roles of miR-211 in humans, and the similarity, and tight functional homology, which was the basis of our next experiments.

Example 5 expression cassette of miR-211 using a Dox-off system: To explore the in-vivo impact of miR-211 decline on cholinergic signaling and seizure susceptibility, we decided to utilize a double transgenic "Tet-Off" system, where engineered mice exclusively express miR-211 from the TRE-insertion in CamK-IIa expressing cells (which are considered in the ART to preferably represent expression in forebrain neurons) and only in the absence of Dox: in order to allowing temporal follow-up of the effects of introducing and removing over-expression. To these means we $1^{st}$ generated a TRE vector for expressing the murine miR-211, by cloning the pre-mmu-miR-211 sequence into a pTRE-tight vector.

Example 6 pTRE-miR-211 transgenic mice: Transgenic founder mice with a genomic insertion for the TRE-vector above generated by pronuclear injection.

Identification of positive founder lines was by tissue-derived-sample based PCR. Two founder lines were maintained for experiment. Founder lines had NO substantial phenotypes.

Example 7

DTg-211 mice carry the CamK2a promoter, followed by a trans-activator (tTa) coding sequence and a pTRE-transgene inducing Doxycycline-suppressible expression of mmu-miR-211 in forebrain neurons and show MiR-211 over-expression in the forebrain but not cerebellum—which was Dox-suppressible:

Progeny double-transgenic mice (dTg-211), (Of TRE-211 and CamK2a tet line) showed over-expressed miR-211 in forebrain tissues taken post mortem, but only in the absence of Doxycycline.

When administered with Dox in drinking water for 6-8 weeks, dTg-211 mice exhibited normally low forebrain miR-211 expression levels, indistinguishable from those in control mice In contrast, Dox withdrawal induced miR-211 accumulation in their frontal cortex, hippocampus and striatum, but not in the cerebellum, essentially as reported for other CamK:Tet mouse lines.

Example 8 transgenic mice expressing miR-211 following a neuronal glial oligodendrocyte OR endothelial promoter:

Transgenic mice expressing the pre-miR-211 (SEQ ID No. X) OR miR-211-5p (SEQ ID No. Y) Can be generated by cloning these sequences following a tissue cell-type specific promoters, such as the CamKII, and as common in the ART. Moreover, using characterized promoters for that are restricted for each specific brain cell type (Neuronal, endothelial, oligodendrocytes OR astrocytes: see Darmanis et al. 2015 and cell type analysis herein) would provide expression which is substantially cell type-specific in the brain, albeit require additional experimentation.

Example 9 transgenic mice expressing miR-211 in a Dox-on manner:
Transgenic mice expressing the miR-211 sing a Dox-on system can be performed by a person of skill in the ART, choosing a Dox-on mouse with brain expression from the publically available strains (E.g. lists in The Jackson Laboratory). Crossing such mice would avoid the need to feed animals with Dox prior to experiment, and would allow the examination of overexpression of a miR-211 sequence (by expressing a miR-211-5p (Seq ID No YY mouse) OR moR-211 as a pre-miR, and as in seq ID No. XX mouse) OR a complementary sequence, OR any sequence which includes the above sequences and would undergo the biogenesis pathway of miRNAs in a mammalian cell.

Example 10

DTg-211 mice have Dox-suppressible expression in timescale of days:
When re-administered with Dox, adult (2-month-old) dTg-211 mice showed miR-211 decline to basal levels in the frontal cortex within 4 days, supporting the applicability of these mice for evaluating temporal attributes of miR-211 decreases in the forebrain.

Example 11

Using the DTg-211 mice with Dox-suppressible expression as a model system for examining EEG-measurable seizures:
In this experimental scheme: DTg-211 mice were administered Dox before and after birth, preventing transgene overexpression during development; and up to age that mice were weaned (3 to 4 weeks after birth). ECoG (EEG) recordings in dTg-211, but not control mice assessing the synchronous neuronal cortical activity after Dox-treatment—which is reminiscent of seizures, and parallel to the decline in miR-211 levels.

Example 12

DTg-211 mice presented ECoG-recorded seizures exclusively after Dox administration:
To directly test if miR-211 decline affects cortical neuronal hyper-excitability, we performed electrocorticography (ECoG) measurements on the mice before and following Dox-mediated miR-211 reduction: ECoG recordings were initiated and 4-6 days after, Dox was re-administered, once again reducing the elevated miR-211 levels. During the subsequent 6 days, ECoG recordings demonstrated spontaneous non-convulsive seizures in six of eight dTg-211 mice but in none of nine control CamK mice receiving similar Dox treatment. Seizures mostly initiated by the $3^{rd}$ or $4^{th}$ day after Dox administration (FIG. 2F), parallel to the decline in miR-211 overexpression. Identified seizures showed a pattern of low frequency (~5 Hz) and sharp activity, without observed motor convulsions.

Example 13

Forebrain miR-211 suppression exacerbates long-lasting PTZ-induced convulsions:
To further address how miR-211 may effect seizure susceptibility we treated dTg-211 mice with Dox for 6 days, and challenged them (and their matched controls) with the seizure-provoking agent PTZ—5 days after Dox has been removed (I.e. when the levels of cortical miR-211 are again elevated) manual convulsions-index scores were elevated in dTg-211 mice, compared to controls.

Example 14

Forebrain miR-211 suppression exacerbated long-lasting PTZ-induced seizures:
ECoG recording shows larger spikes/min counts, reflecting seizure-susceptibility in PTZ-exposed dTg-211 mice compared to CamK controls. Also parameters such as Number of seizures; Latency from PTZ injection to $1^{st}$ spike; and number of seizure-events by Neuronal-networks analysis; as well as the latency to first seizure were are suggestive to higher susceptibility and lower threshold for seizures, in this state.

Example 15

Forebrain miR-211 suppression effects TGF-β signaling which is related to seizures (Via TGFBR2):
Given the reported role of TGFβ signaling in epileptogenesis, we next examined if the TGFβ pathway genes which change following status epilepticus were modified in the epilepsy-susceptible dTg-211 mice following Dox. Non-Dox-treated frontal dTg-211 cortices showed two-fold lower TGFBR2 transcript levels compared to controls, alongside ~40% reduced TGFBR2 protein. This finding corresponded to the 3'-UTR of the murine TGFBR2 gene showing seed sequence complementarity with the mature mmu-miR-211, and an in-vitro (psi-check luciferase based) assay showed direct downregulation of the murine TGFBR2 3'-UTR reporter by mmu-miR-211, validating this miR-target link. Reciprocally, administration of Dox induced a step-wise 4-fold increase in TGFBR2 mRNA within 4 days.

Example 13

RNA sequencing from frontal cortex samples of Dox treated/untreated dTg-211 mice and controls to address transcriptional changes:
To explore if TGFBR2 pathway genes are globally changed, we turned to unbiased RNA-sequencing of dTg-211 cortical tissue RNAs (without and with Dox suppression of miR-211 overexpression) as compared to matched control tissues. The cDNA libraries showed overall similar sequencing depth, reads distribution across expression level and inter-related tag-wise normalized variance and expression levels.
Comparing dTg-211 brains before and after 5 days of Dox administration showed substantially higher numbers of differentially expressed genes than comparing naïve dTg-211 brains to CamK-controls, suggesting that Dox-induced suppression of miR-211 overexpression may entail an extensive physiological change.
miR-211 target transcripts (as predicted in silico by the TagretScan algorithm) showed significant albeit mild increases and decreases following Dox administration. Such as to suggest that the bulk of transcriptome changes induced by miR-211 perturbations occurred in secondarily affected transcripts, and that the transcriptional footprint of miR-211 reduction was greater than that of its sustained over-expression.

Example 14

RNA sequencing from dTg-211 with/without Dox and controls finds Dox specific changes in TGFBR2 related genes:

Numerous TGFβ pathway genes that were modified 12 hr following status epilepticus (39) were also changed following Dox, either by up- or down-regulation (FIG. 30), including the Myc Proto-Oncogene Protein (MyC), the Chordin (chrd) Inhibitor of DNA Binding 2, HLH Protein (id2) and SMAD Family Members 1 and 9 (smad1, smad9), suggesting that the Dox-induced release of TGFBR2 from miR-211-mediated suppression impacted forebrain TGF-β signaling.

Example 15

RNA sequencing from dTg-211 with/without Dox and controls finds Dox specific changes in cell-type marker genes:

Expressed genes characteristic of neurons, astrocytes, oligodendrocytes and their progenitor cells (OPCs), microglia and endothelial cells were described in Darmanis, et al. (2015) none of the cell type marker groups showed changes in dTg-211 brains compared to controls. However, comparing dTg-211 transcripts in brains with and without Dox demonstrated that 19 of 21 endothelial cell markers (and in contrast, none of the other cell type gene-marker-groups) showed an increase following Dox administration (P<0.05, P val by perturbation analysis, see Methods). Thus, miR-211 reaction to Dox appeared to potentiate endothelial gene expression, predicting functional relevance for neurovascular unit activities.

Example 16

RNA sequencing from dTg-211 with/without Dox and controls finds specific and functionally directional expression changes in cholinergic genes:

The excitatory muscarinic ACh receptor-5 (mAChR5) a positive effector of cholinergic synaptic transmission was elevated by 4-fold. Likewise, the excitatory nAChRα-1 neuronal nicotinic receptor and α-5 nicotinic receptor (Chrna5) the stress-inducible muscarinic m1 receptor and the ionotropic α-7 nicotinic receptor (Chrna7), responsible for post- and presynaptic excitation and blocker of inflammation, were all elevated. In contrast, the metabotropic muscarinic ACh receptors-4 and -2 (mAChR4, mAChR2) were both two-fold reduced following Dox administration. MAChR4 is located on both pre- and post-synaptic sites in brain cholinergic synapses, and exerts inhibitory effects on synaptic firing with a role in locomotion. Additionally, we noted increases in butyrylcholinesterase (BChE) which hydrolyzes ACh in the brain alongside AChE and is elevated in AD brains. In contrast, we noted decrease of ATCAY/BNIP-H, an ataxia-related brain-specific scaffold protein, which was recently found to recruit Choline Acetyltransferase (ChAT) to neurite terminals, and promote cholinergic signaling.

Of note: Dox-induced downregulation of cholinergic receptors suppressing synaptic transmission: CHRM2 and CHRM4 (M2 and M4); and upregulation of facilitators CHRM5 (M5), CHRNA5 and CHRNA7 (α5 and α7).

Example 16

MiR-134 upregulation in dTg-211 mice following Dox administration paralleled the timeframe of seizure induction:

dTg-211 mice—4 days following Dox administration presented a 4-fold increases in the forebrain levels of miR-134 as compared to CamK controls. miR-134 is known to be causally involved with the induction of convulsive seizures. This timeframe parallels that of miR-211 expression level changes and the seizure induction in this model, as described above.

Example 17

In a second mouse model—mice overexpressing the non-synaptic cholinergic enzyme AChE-R: the higher propensity and shorter latency to SE following Pilocarpine injection, was evident alongside miR-211 reduction and miR-134 elevation.

To address the set of phenomena we noted in miR-211 expressing mice we decided to examine a second mouse model we and others have developed in the past: which may provide a wider base to our conclusions regarding the functions of miR-211; AND concord with hypothesis regarding the role of extra-synaptic cholinergic imbalance and feedback affect on miR-211 expression and the risk of epilepsy.

This second transgenic mice model comprises mice transgenically expressing the AChE-R (TgR) this enzyme is the soluble, non-synaptic stress-induced splice variant of AChE. Also, in this transgenic model the 3'-untranslated region (UTR) which contains the miR regulatory element (MRE) had been deleted Of note, is has been shown that TgR mice, which constitutively overexpress AChE-R (that catalyzes ACh breakdown in extra-synaptic sites) show chronic stress behaviors, are hyper-sensitized to nicotine administration.

We noted that these mice experienced higher susceptibility to seizures, manifested as larger fraction of mice presenting full status epilepticus after pilocarpine injection.

This was accompanied by shorter latency until status epilepticus was observed, reduced miR-211 expression in the hippocampus and frontal cortex compared to controls, and overexpression of miR-134 in the prefrontal cortex and hippocampus. Thus, modified cholinergic regulation in TgR mice elevated both forebrain miR-211 and miR-134 levels and exacerbated susceptibility to epileptic seizures.

Example 18 memory phenotypes in miR-211 expressing mice and hsa-miR-211 overexpression in brains of AD patient:

In the MWM dTg-211 mice shows reduced learning ability, as assessed by time to reach platform, in the 1st and 2nd training days (dTg-211 mice V.s controls). In addition when assessing search strategy scores—Fewer trials of dTg-211 mice in the last days showed focal or directed strategy. Loss of preference of the platform quadrant, is considered to be reflecting an impaired reference memory for dTg-211 compared to CamK mice in probe trials.

We find these observation to concord with the higher miR-211 levels (~2-fold) we noted in post-mortem Alzheimer's entorhinal cortices compared to non-demented controls (n=7 each, Netherland Brain bank) $p<0.05$, Student's t-test.

Example 18

Intracranial Injection of a pTRE-miR-211 vector to a CamKII transgenic mouse to induce local miR-211 modification by administering Dox:

To examine local effects of miR-211 overexpression and subsequent reduction the pTRE-211 plasmid including SEQ ID No. 3 (mmu-pre-miR-211) is performed by methods known in the ART. Concentrations of vectors and solutions for such an injections are standard in the ART (see Lowery, R. L., Majewska, A. K. Intracranial Injection of Adeno-associated Viral Vectors. J. Vis. Exp. (45), e2140, doi: 10.3791/2140 (2010).

Example 19

Intracranial Injection of a miR-211 LNA mimetic to examine for protection against seizures and change in seizure threshold:

To examine local effects of miR-211 increase an Intracranial Injection of a miR-211 LNA mimetic is performed by methods known in the ART. Concentrations of LNA and solutions for such an injections are standard in the ART (Ernesto Caballero-Garrido et al., Journal of Neuroscience, 2015).

Example 20

Intracranial Injection of a miR-211 LNA sponge to induce a reduction in susceptibility to seizures:

To examine local effects of miR-211 decrease an intracranial injection of a miR-211 LNA sponge is performed by methods known in the ART. (Ernesto Caballero-Garrido et al., Journal of Neuroscience, 2015).

Example 21 systemic injection of a miR-211 LNA mimetic to examine for protection against seizures in a blood brain-barrier compromised animal:

To the potency of miR-211 by systemic injection to a TBI model animal specifically a blood brain-barrier compromised animal—systematic injection of a miR-211 LNA mimetic is performed. Systemic injection and blood brain-barrier compromised animal models are known in the ART in detail.

---

The invention claimed is:

1. A method for treating epilepsy by reducing the chance for seizures in a brain of a mammal in need thereof, the method comprising: introducing into said brain of said mammal, an oligonucleotide with the nucleic acid sequence of miR-211 by (i) administering to said mammal a non-endogenously synthesized mimetic oligonucleotide; or (ii) introducing into cells of said brain an expression cassette, expressing the nucleic acid sequence of miR-211, wherein the nucleic acid sequence of miR-211 provides a reduction in hyper-synchronization or non-convulsive seizures in the mammal.

2. The method of claim 1, wherein said introducing of said oligonucleotide is done by administering to said mammal an externally synthesized oligonucleotide.

3. The method of claim 2, wherein said oligonucleotide is a miR-211 mimetic molecule.

4. The method of claim 3, wherein said mimetic molecule is selected from a group consisting of locked nucleic acid (LNA), 2-O-methyl-blocked, Morpholino and phosphorothioate oligonucleotides.

5. The method of claim 2 wherein said oligonucleotide is selected from the group consisting of: SEQ ID No. 1, SEQ ID No. 2, SEQ ID No. 3, SEQ ID No. 4, SEQ ID No. 5, SEQ ID No. 6.

6. The method of claim 5 wherein said oligonucleotide is selected from the group consisting of: SEQ ID No. 1, SEQ ID No. 2, and wherein the mammal is selected from the group of human, non-human primate, mouse and rat.

7. The method of claim 1, wherein introducing said oligonucleotide is done by transgenic modification of non-human organism.

8. The method of claim 1, wherein said brain is the brain of a human individual suffering from a seizure related condition.

9. The method of claim 8, wherein said seizure related condition is epilepsy.

10. The method of claim 9, wherein said seizure related condition is refractory OR intractable epilepsy.

11. The method of claim 8, wherein said brain is the brain of an individual suffering from acute traumatic stress.

12. A method for treating seizures in a mammalian brain comprising: administering miR-211 to said mammalian brain.

13. The method of claim 12 wherein said administering elevates functionality of miR-211 in said mammalian brain.

14. The method of claim 12 wherein said administering elevates the abundance of miR-211 in said mammalian brain.

15. The method of claim 1, wherein administering involves providing the miR-211 by adding it to food that is eaten by the mammal, or injecting the miR-211 into the brain of the mammal.

* * * * *

SEQUENCE LISTING

```
<160> NUMBER OF SEQ ID NOS: 6

<210> SEQ ID NO 1
<211> LENGTH: 22
<212> TYPE: RNA
<213> ORGANISM: Artificial Sequence
<220> FEATURE:
<223> OTHER INFORMATION: miRNA

<400> SEQUENCE: 1
uucccuuugu cauccuuugc cu                                           22

<210> SEQ ID NO 2
<211> LENGTH: 22
<212> TYPE: RNA
<213> ORGANISM: Artificial Sequence
<220> FEATURE:
<223> OTHER INFORMATION: miRNA

<400> SEQUENCE: 2
uucccuuugu cauccuucgc cu                                           22

<210> SEQ ID NO 3
<211> LENGTH: 106
<212> TYPE: RNA
<213> ORGANISM: Artificial Sequence
<220> FEATURE:
<223> OTHER INFORMATION: miRNA

<400> SEQUENCE: 3
gugcuuggac cugugaccug ug                                           22 ggcuucccuu ugucauccuu ugc                                          45 cuaggccucu gagugaggca ag                                           67 gacagcaaag gggggcucag ug                                           89 gucaccucua cugcaga                                                106

<210> SEQ ID NO 4
<211> LENGTH: 110
```

```
<212> TYPE: RNA
<213> ORGANISM: Artificial Sequence
<220> FEATURE:
<223> OTHER INFORMATION: miRNA

<400> SEQUENCE: 4
ucaccuggcc augugacuug ug                                         22 ggcuucccuu ugucauccuu cgc                                        45 cuagggcucu gagcagggca gg                                         67 gacagcaaaggggugcucaguu                                           89 gucacuucccacagcacggag                                           110

<210> SEQ ID NO 5
<211> LENGTH: 21
<212> TYPE: RNA
<213> ORGANISM: Artificial Sequence
<220> FEATURE:
<223> OTHER INFORMATION: miRNA

<400> SEQUENCE: 5
gcaaggacag caaagggggg c                                          21

<210> SEQ ID NO 6
<211> LENGTH: 21
<212> TYPE: RNA
<213> ORGANISM: Artificial Sequence
<220> FEATURE:
<223> OTHER INFORMATION: miRNA

<400> SEQUENCE: 6
gcagggacag caaaggggug c                                          21
```